United States Patent [19]

Flinchbaugh

[11] Patent Number: 4,916,915

[45] Date of Patent: Apr. 17, 1990

[54] METHOD OF AND SYSTEM FOR DETERMINING REFRIGERANT/LUBRICANT RATIO WITHIN ENCLOSED FLOW APPARATUS

[75] Inventor: David E. Flinchbaugh, Orlando, Fla.

[73] Assignee: Murray Corporation, Cockeysville, Md.

[21] Appl. No.: 231,382

[22] Filed: Aug. 12, 1988

[51] Int. Cl.$^4$ .............................................. G01K 13/00
[52] U.S. Cl. .................................. 62/129; 73/61.1 R
[58] Field of Search ................. 62/125, 126, 127, 129, 62/192, 193; 73/32 A, 61 R, 61.1 R, 64; 340/621

[56] References Cited

U.S. PATENT DOCUMENTS

| | | | |
|---|---|---|---|
| 3,283,562 | 11/1966 | Heisig et al. | 73/24 X |
| 3,413,595 | 11/1968 | Babikov et al. | 340/5 |
| 3,738,118 | 6/1973 | Jacobs | 62/192 |
| 3,844,163 | 10/1974 | Di Leo | 73/67.5 R |
| 4,090,371 | 5/1978 | Keane | 62/129 |
| 4,122,713 | 10/1978 | Stasz et al. | 73/194 A |
| 4,138,879 | 2/1979 | Liebermann | 62/129 X |
| 4,522,068 | 6/1985 | Smith | 73/32 A |

Primary Examiner—Harry B. Tanner
Attorney, Agent, or Firm—Leonard Bloom

[57] ABSTRACT

A system for and method of measuring refrigerant-to-lubricant ratio of liquid within a conduit having a wall and forming part of an enclosed air conditioning refrigerating apparatus which includes a compressor, an evaporator and a condenser. The system involves a first transducer for generating at least one pulse of ultrasonic energy which is coupled via the wall into a path of substantially predetermined length within the liquid. The least one pulse of ultrasonic energy is coupled from the end of the path via the wall and received by a second transducer. Circuitry responsive to the at least one ultrasonic pulse as transmitted and received determines velocity of the ultrasonic pulse within the liquid as a measure of the refrigerant-to-lubricant ratio. The method includes the steps of generating a pulse of ultrasonic energy, coupling the pulse of ultrasonic energy into the path of predetermined length within the liquid, and coupling the pulse of ultrasonic energy from the end of the path of predetermined length within the liquid. The ratio is derived from determining the velocity of the ultrasonic pulse within the liquid from its transit time along the path of predetermined length.

12 Claims, 5 Drawing Sheets

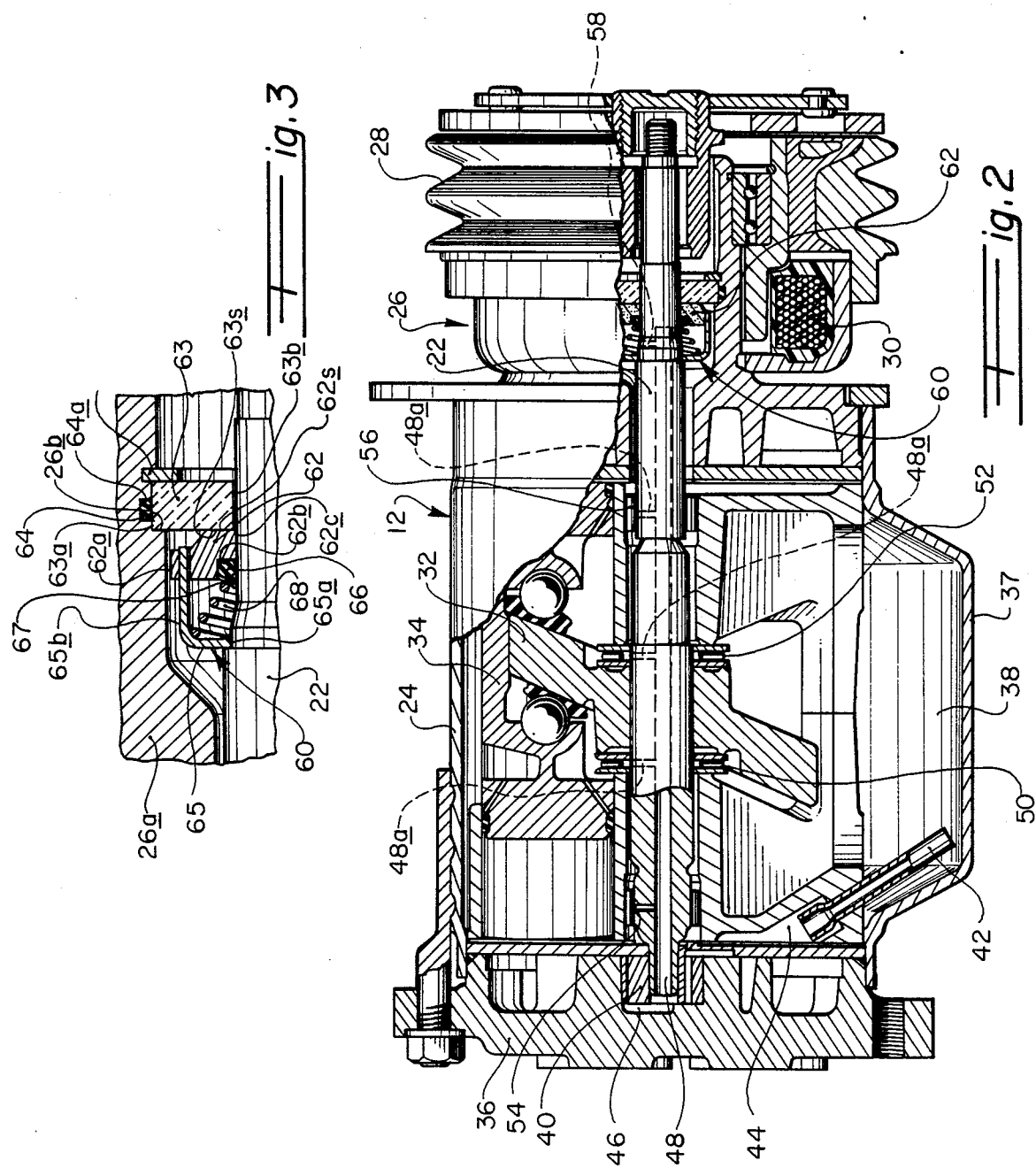

METHOD OF AND SYSTEM FOR DETERMINING REFRIGERANT/LUBRICANT RATIO WITHIN ENCLOSED FLOW APPARATUS

BACKGROUND OF THE INVENTION

1. Field of the Invention

The present invention relates to the air conditioning and refrigeration arts and, more particularly, to a method of and to a system for measuring density of a liquid mixture in an enclosed flow air conditioning or refrigeration apparatus to determine the refrigerant/lubricant ratios of the liquid flowing therein.

2. Description of the Prior Art

A method and an apparatus disclosed in U.S. Pat. No. 4,522,068 to George E. Smith granted June 11, 1985 and entitled "Ultrasonic Densitometer for Liquid Slurries" utilizes the leading edge of a received compression wave resulting from a transmitted pulse into the liquid slurry whose density is being measured. A quantity of the liquid is isolated between a transmitting transducer and a receiving transducer, the two transducers being set at a predetermined distance from one another. Pulses at a predetermined ultrasonic frequency are used to drive the transmitting transducer. A latching output signal is produced with the development of each transmitted pulse and an unlatching output signal is produced with the receipt of the leading edge of the compression wave relating thereto as it is received by the receiving transducer. The time between the latching and the unlatching occurrences is determined, in digital fashion, using a high frequency counting scheme. The count is correlated against an empirically developed standard as an indication of the density of the slurry. On its face, the patent of Smith does not apply to determining refrigerant/lubricant ratios in enclosed flow air conditioning or refrigeration apparatus.

A method of and an apparatus for testing fluids is disclosed in U.S. Pat. No. 3,283,562 granted November 8, 1966 to Charles H. Heisig et al. and entitled "Fluid Testing by Wave Energy", wherein a limited portion of the wall of a liquid containing cavity is caused to vibrate mechanically in such fashion as to propagate acoustic wave energy in the liquid. Consequently, this acoustic wave energy is coupled, by a liquid, into the wall of the cavity to cause mechanical vibration thereof that represents some part of the original mechanical vibrations, but of a character determined, in part, by the acoustic properties of the liquid, variation in such properties modulating the acoustic wave energy propagated in the liquid. The vibrations in the wall, coupled thereto from the liquid, are sensed and demodulated in order to obtain information as to one or another of the acoustic properties, such as gas content in the form of a bubble or a plurality of bubbles or specks of gas, the gaseous component of liquid having a marked modulating effect on acoustic wave energy propagated in the liquid. No application is seen in using such techniques for the purpose of determining refrigerant/lubricant ratios in an enclosed flow air conditioning or refrigeration apparatus.

Refrigeration and air conditioning apparatus failure with few exceptions, is due to one of three conditions. These are leakage into or out of the apparatus, circulation malfunction and improper compressor lubricant oil conditions. The problems are especially significant in vehicle air conditioning systems, one such typical system being disclosed in U.S. Pat. No. 3,738,118 granted June 12, 1973 to James W. Jacobs and entitled "Means for Lubricating Vehicle Air Conditioning Compressor Shaft Seals". Of the above-mentioned three causes of malfunction or failure, the last, inadequate compressor lubrication, is the most frequent and most often the cause of catastrophic system malfunction. Refrigeration and air conditioning compressor lubrication is unique in that the refrigerant liquid mixes with the lubricating oil and creates lubrication hazards not commonly encountered in other classes of high speed rotating machinery.

The quantity of refrigerant in a typical apparatus may be greater than the quantity of lubricating crankcase oil in the apparatus compressor. Ordinarily, a portion of the crankcase oil is carried around the refrigeration system by the refrigerant. However, if too much oil leaves the compressor crankcase, or if too much oil is suddenly returned with the refrigerant to the compressor through the compressor inlet, failure of the compressor may result.

Should the liquid refrigerant replace the oil in the compressor crankcase during an inversion of the oil and refrigerant, which may occur with certain commonly used refrigerants when a sufficiently low crankcase temperature is attained, the oil in the compressor will be nearly completely swept out of the compressor and all lubricated interaction of the moving parts and bearing surfaces of the compressor will quickly be lost. Rapid catastrophic failure of the compressor and of the system results.

Moreover, the refrigerant used in many small refrigerating apparatus and in small air conditioning apparatus, such as in automobiles and the like, tends to leak out of the apparatus over periods of time, causing too much lubricant to be present in the circulating liquid, resulting in a reduced cooling capacity. When the refrigerant is replaced, one needs to take care so that the proper refrigerant/lubricant ratio range is achieved and is not exceeded.

SUMMARY OF THE INVENTION

An object of the present invention is to provide a method of and a system for testing the circulating liquid in a refrigerating or air conditioning apparatus to determine the refrigerant/lubricant ratio of the liquid to aid in assuring that the ratio is within acceptable limits.

Another object of the present invention is to provide a method of and a system for monitoring the refrigerant/lubricant ratio of circulating liquid within a refrigerating or air conditioning apparatus so that the ratio can be maintained within acceptable limits.

A further object of the present invention is to provide a method of and a system for reducing the probability of or avoiding failure of an air conditioning or refrigerating apparatus because of unacceptable refrigerant/lubricant ratios.

In one vantage point, the present invention in its apparatus aspect can be seen as a system for measuring refrigerant-to-lubricant ratio of liquid within a conduit having a wall and constituting a portion of an air conditioning or refrigerating system which includes a compressor, an evaporator and a condenser. The system includes means for generating at least one pulse of ultrasonic energy. Coupling means is provided for coupling the at least one pulse of ultrasonic energy via the wall into a path of substantially predetermined length within the liquid constituting a liquid mixture of lubricant and refrigerant. Coupling means is provided to couple the at least one pulse of ultrasonic energy, as received at the end of the path, from the path via the wall. Instrumentalities responsive to the at least one ultrasonic pulse as transmitted and received determine velocity of the ultrasonic pulse within the liquid.

The instrumentalities responsive to the at least one ultrasonic pulse as transmitted and as received may include readout means calibrated in percent of lubricant in the liquid by weight.

From a method vantage point, which can be realized using the system of the present invention, the present invention can be viewed as a method for measuring refrigerant-to-lubricant ratio of liquid in an air conditioning or refrigerating system. The method involves generating a pulse of ultrasonic energy, coupling the pulse of ultrasonic energy into a path of predetermined length within the liquid constituted by a liquid mixture of lubricant and refrigerant, coupling the pulse of ultrasonic energy from the end of the path of predetermined length within the liquid, and determining the velocity of the ultrasonic pulse within the liquid from its transit time along the path of predetermined length.

The method may desirably include determining, from the velocity, the percent of lubricant in the liquid by weight.

The system of the present invention, as well as the method which can be carried out therewith, is designed to be especially useful for measuring refrigerant/lubricant ratios in small air conditioning and refrigerating systems. Although useful for many industrial process and process control applications, this illustration is especially important. There is currently no effective technique to determine how much compressor-oil is circulating with the refrigerant in automotive and small fixed location air conditioners. The refrigerant is known to leak from these pressurized systems over some period of time and must be replaced. Also the proper cooling and lubrication of the compressor requires the correct range of refrigerant/oil charge and ratio, as noted above.

The novel features characteristic of the present invention are set forth with particularity in the appended claims. The invention itself, however, both as to its organization and method of operation, together with further objects and advantages thereof, is best understood by reference to the following description taken in conjunction with the accompanying drawings.

BRIEF DESCRIPTION OF THE DRAWINGS

FIG. 2 is a partial, enlarged cross-sectional view of a conventional compressor which may be used in the refrigerating or air conditioning apparatus of FIG. 1, partially illustrating the flow of lubricant therein.

FIG. 3 is an enlarged, fragmentary portion of the compressor of FIG. 2, showing the structure of its shaft sealing assembly in detail.

DETAILED DESCRIPTION OF THE PREFERRED EMBODIMENTS

Figure 1:
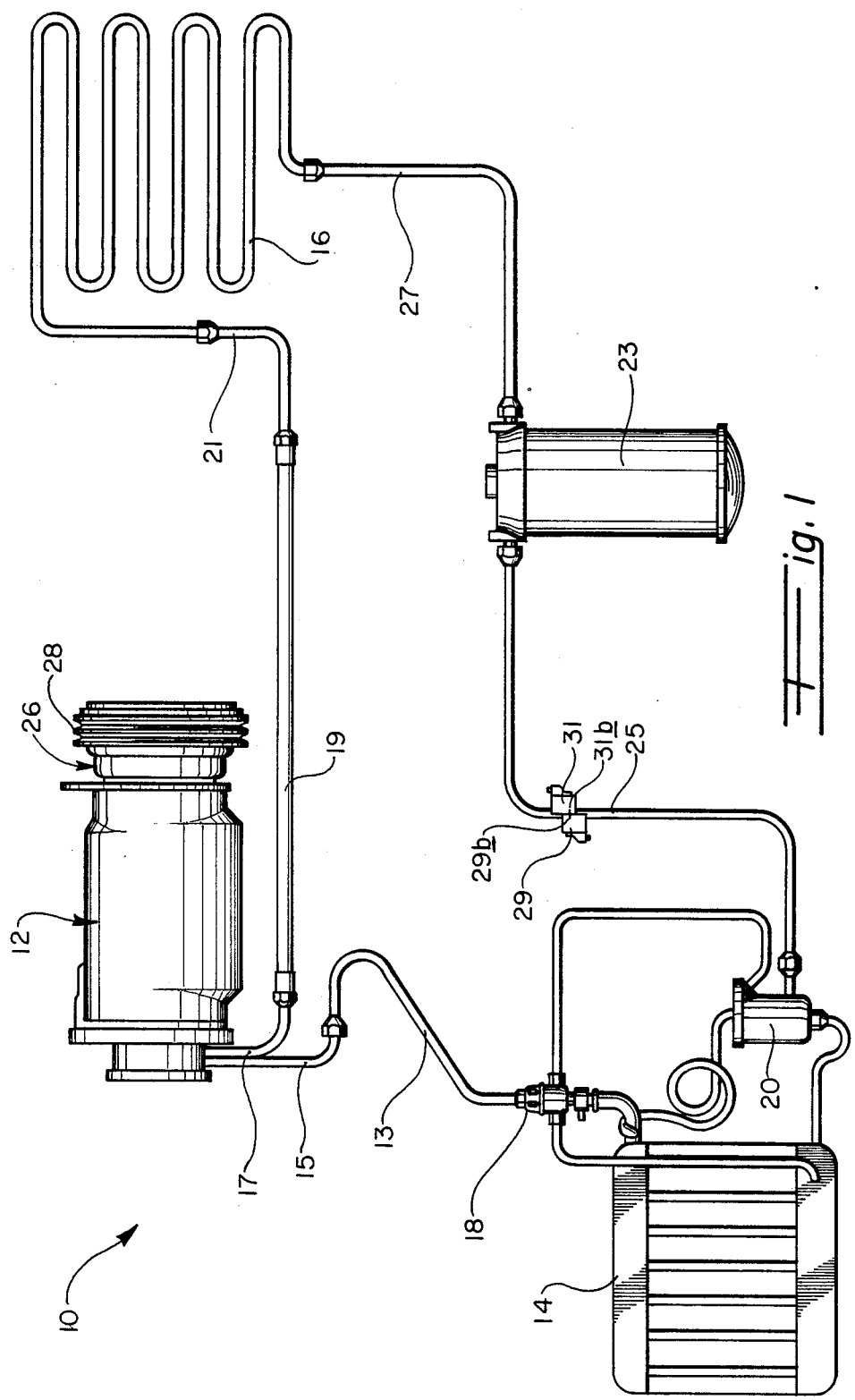
FIG. 1 is a schematic diagram showing the liquid circuit of a conventional refrigerating or air conditioning apparatus, such as used in a vehicle, the placement of transducers about a conduit in accordance with a feature of the present invention being illustrated.

With reference to FIG. 1, a conventional air conditioning liquid circuit 10 is illustrated as including a compressor 12, series connected compressor inlet conduits 13 and 15, an evaporator 14 and a condenser 16, the condenser being connected to the outlet of the compressor via series connected conduits 17, 19 and 21. The compressor 12 is driven from a driving pulley assembly 28 via a clutch 26, or conventional arrangement. A suction throttling valve 18 is in the liquid circuit between the compressor 12 and the evaporator 14, while an expansion valve 20 is utilized in series with a dehydrator receiver 23 between the evaporator 14 and the condenser 16, the expansion valve 20 being coupled to the receiver 23 via a conduit 25. The receiver 23 is in liquid communication with the outlet from the condenser 16 via a conduit 27. A pair of transducer housings 29 and 31 are removably coupled to the conduit 25 in accordance with the present invention. The housings 29, 31 are provided with respective alignment markings 29b, 31b.

The compressor 12 is shown in detail in FIG. 2 wherein a shaft 22 extends through a compressor casing 24 and is driven by the electrically engaged clutch shown generally at 26. The clutch 26 includes the driving pulley assembly 28 that is selectively engaged with the shaft 22 when a solenoid coil 30 of the electric clutch 26 is energized. The shaft 22 receives a swash plate 32 fixed for rotation therewith and reciprocating dual acting piston 34 circumferentially spaced about the shaft 22 within the housing 24. The reciprocating movement of the double acting piston 34 pressurizes liquid in the housing 24 for discharge through a passageway in an end plate 36 into the outlet conduit 17 (FIG. 1). Liquid is also supplied to the compressor 12 through a passageway in the end plate 36 from the inlet conduit 15 (FIG. 1), as is conventional. The housing 24 includes a distended portion 37 defining a sump 38 which collects an oil and refrigerant mixture for circulation through the compressor shaft 22 lubricating its associated bearings and seals, the circulation being provided by a lubricating gear pump assembly 40 secured at the left end of shaft 22 viewed in FIG. 2. Lubricating oil and refrigerant are drawn from the sump 38 through conduit 42 to a passage 44 connecting with the inlet side of gear pump 40. The pump 40 discharges the pressurized mixture into a chamber 46 from which it flows through an axial passage 48 in shaft 22 to lubricate needle thrust bearing assemblies 50 and 52 as well as radial needle bearing assemblies 54 and 56 through radial passages 48a. The oil mixture also exits axial passage 48 via an orifice 58 to lubricate a shaft seal assembly 60. The oil supplied to the aforementioned bearings and the seal assembly 60, returns to sump 38 via passages (not shown) as is conventional.

The shaft seal assembly 60 is best illustrated in FIG. 3 and includes a carbon seal element 62 fixed to rotate with the shaft 22 and a ceramic seal element 63 nonrotatably mounted within the clutch housing portion 26a against a shoulder 26b by a snap ring 26c. An o-ring 64 is received within a notch 64a and sealingly engages the outer circumferential surface 63a of the seal element 63 preventing flow of a mixture of lubricant and refrigerant between the housing and element 63. The inner circumferential surface 63b of element 63 is retained out of engagement with the shaft 22 as shown. A cage 65, formed of a suitable metal, contains an aperture 65a having at least one flat driving surface engaging a like surface of shaft 22, neither of which surfaces are shown, when the cage is placed on the shaft. The flat surfaces provide a driving engagement between the cage 65 and shaft 22. The carbon seal element 62 has a notch 62a receiving end 65b of the cage 65 so that the element 62 rotates with the cage and the shaft 22. The carbon seal element 62 also contains a circumferential notch 62b at its inner surface 62c which receives an o-ring seal 66. An annular washer 67 is biased to compress the o-ring seal 66 into sealing contact with the shaft 22 by a conical helical spring 68 placed in compression between cage 65 and the washer 67. The carbon element 62 is mounted for rotation with the compressor shaft 22 and is sealed at its inner surface 62c by o-ring 66 under the influence of spring 68 preventing flow of liquid between the element 62 and shaft 22. The ceramic seal element 63 is stationary and is sealed at its outer surface 63a by o-ring 64. The carbon element 62 has a seal face 62s that is biased toward a like face 63s of the ceramic element 63, so that these faces cooperate to support a thin sealing lubricant film therebetween providing the liquid seal between 40 these elements. A thin film of lubricant or mixture of lubricant and refrigerant is provided between these faces at all times to prevent frictional engagement thereof and actually provide the desired seal during operation of the compressor.

Based on data obtained with radiographic, ultrasonic, magnetic and optical noncontact density flow measurement techniques and instrumentation, an exemplary novel method of and system for determining refrigerant/lubricant ratio within enclosed flow apparatus measuring liquid density changes in opaque, enclosed flow systems have been developed in accordance with the present invention. As illustrated in FIG. 1, a housing 29 containing a pulsed piezoelectric transducer 29a (FIGS. 4A, 4B) is positioned on the conduit 25 to transmit ultrasonic waves through the wall thereof and into the liquid medium made up of a mixture of lubricating oil and refrigerant. The pulsed piezoelectric transducer 29a is one of an opposing pair of single-pair in line pulse transducers 29a and 31a, the transducer 31a being housed within the housing 31. The housings 29, 31 and transducers 29a, 31a are in the form of single unit clamp-on device shown in more detail in FIGS. 4A, 4B. While the exemplary preferred embodiment, an opposing of transducers 29a and 31a are illustrated as being coupled to the conduit 25, it is to be understood that a single pulse-echo transducer configuration may be employed, if desired. In this case a single transducer would be coupled to the conduit 25, a reflecting inner surface area of the conduit directing the pulsed energy back toward the single transducer, the path distance in this case being double the length of the path defined in the arrangement in which a pair of transducers are used. Transit time (velocity) is a function of the density of the medium, which is a function of ratio of lubricant-to-refrigerant or, to state relationship somewhat differently, by the weight percent of lubricant in the circulating liquid. Calibration is accomplished using prior knowledge of physical constants of the medium and its environment (e.g. pressure, temperature, chemical constituents, densities of the individual constituents and the like). Empirical observations indicate that the velocity is directly, linearly related to weight percent (%) of lubricant in the circulating liquid. The system described allows frequent monitoring of density and density changes in the system because of the effects thereof on detected ultrasonic waves.

Figure 4A:
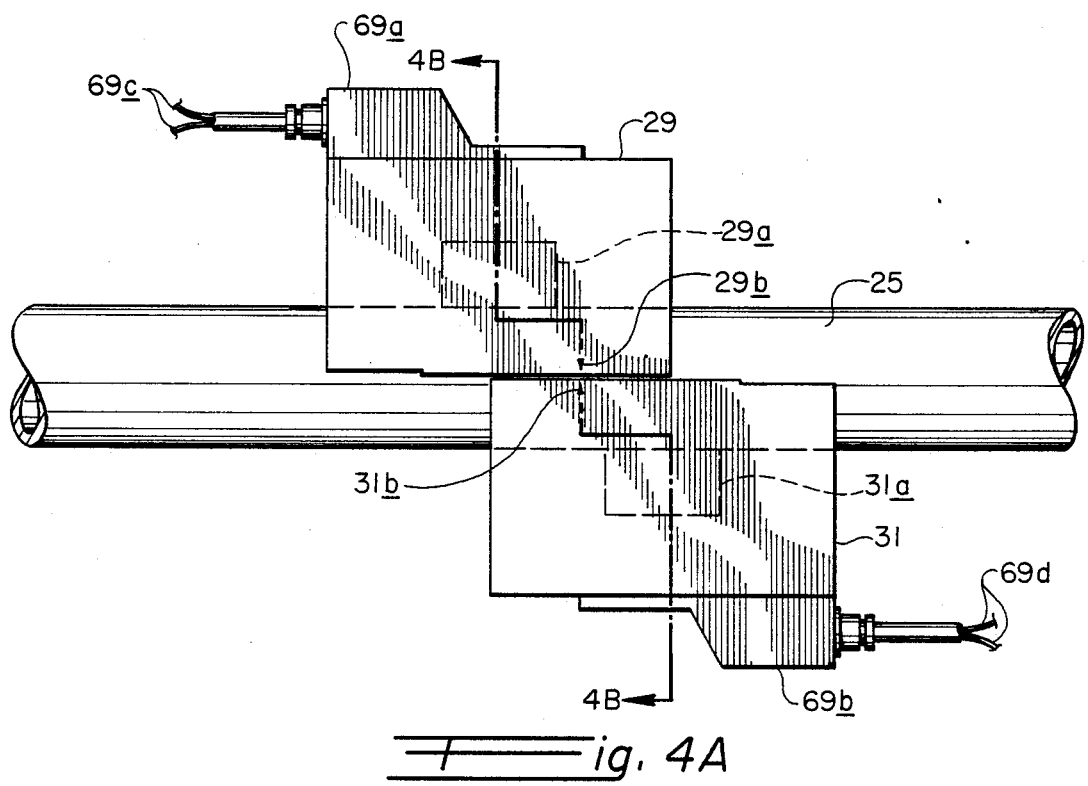
FIG. 4A is an enlarged view of a portion of the conduit of FIG. 1 about which the transducers are placed, the housings of the transducers show the relative placement of the two transducers relative to one another and to the conduit and the liquid flowing therein.
Figure 4B:
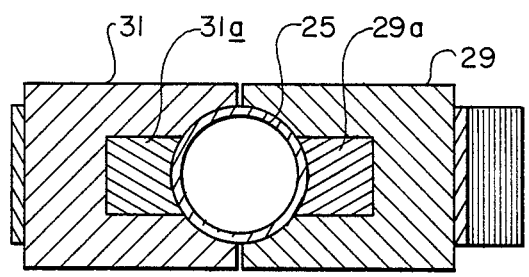
FIG. 4B is a cross-sectional view of the conduit, housing and transducers of the arrangement shown in FIG. 4A, the section having been taken along section line 4B—4B in FIG. 4A.

In practicing the present invention, the transducers 29a and 31a are positioned circumferentially about the conduit 25, as best seen in FIGS. 4A, 4B, with the alignment markings 29b, 31b aligned with one another. The respective transducers 29a and 31a are desirably fixed with a clamp-on housing defined in part by the housings 29, 31, which includes input and output wiring housings 69a and 69b to and from which respective wiring lead pairs 69c and 69d extend for supplying respectively electrical energy to and receiving electrical energy from the respective transducers 29a and 31a. The transducers 29a and 31a and the housings 29, 31 can, as was established in a test of the system of the present invention, be a portable assembly available commercially from *Controlotron Corp.* under the designation "961 Transducer Wiring Housing and Block". In order to effect good transfer of acoustic energy into and from the liquid mixture within the conduit 25, a coupling compound is desirably placed between the respective transducers 29a and 31a and the conduit 25. A suitable compound is commercially available from *Controlotron Corp.* under the designation "Controlotron Coupling Compound No. CC1114". The transducer 29a effects axial beam injection of ultrasonic energy into the conduit 25.

Figure 5:
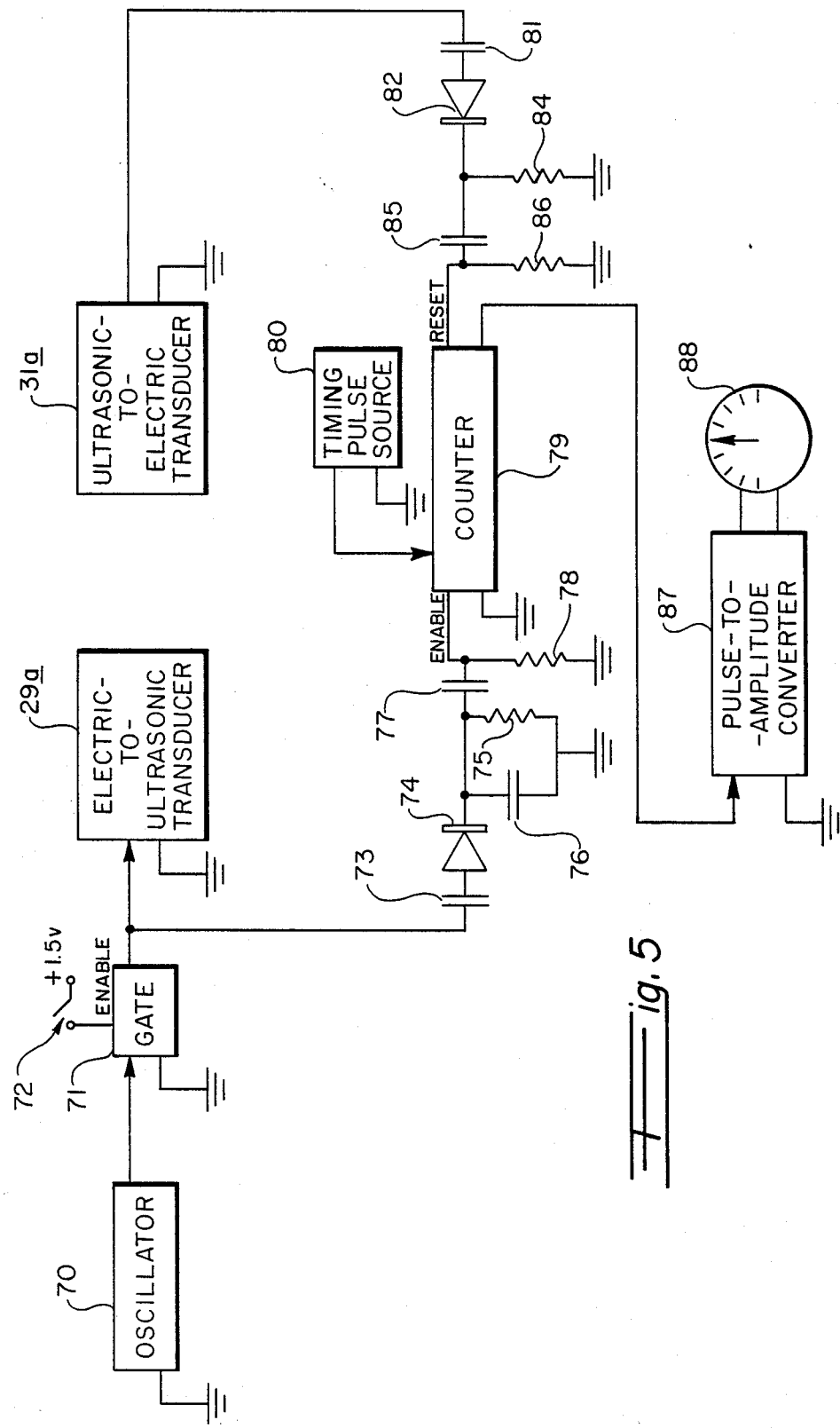
FIG. 5 is a schematic diagram of a system for determining the refrigerant/lubricant ratio of the liquid within a conduit which forms part of the apparatus shown n FIGS. 1, 4A and 4B in accordance with an exemplary embodiment of a system constructed in accordance with the present invention, in its system aspect, and suitable for carrying out the invention in its method aspect.

An exemplary circuit diagram of a system for effecting a determination of the refrigerant-to-lubricant ratio of the liquid, flowing in the vehicle air conditioning apparatus illustrated in FIGS. 1–3, as well as similar air conditioning and refrigerating systems is shown in FIG. 5. The system includes an oscillator 70 which produces an a. c. electrical output signal having a frequency in the ultrasonic range. A gate 71 is operatively arranged to receive the electrical output from the oscillator 70, its enable input terminal being connected to a mechanically biased switch 72 which, when momentarily closed, supplies a positive 1.5 v control signal to the gate 71, allowing a short pulse of the electrical signal from the oscillator 70 to be supplied, as an energizing input, to the electric-to-acoustic transmitting transducer 29a (also illustrated in FIGS. 1, 4A and 4B).

Figure 6:
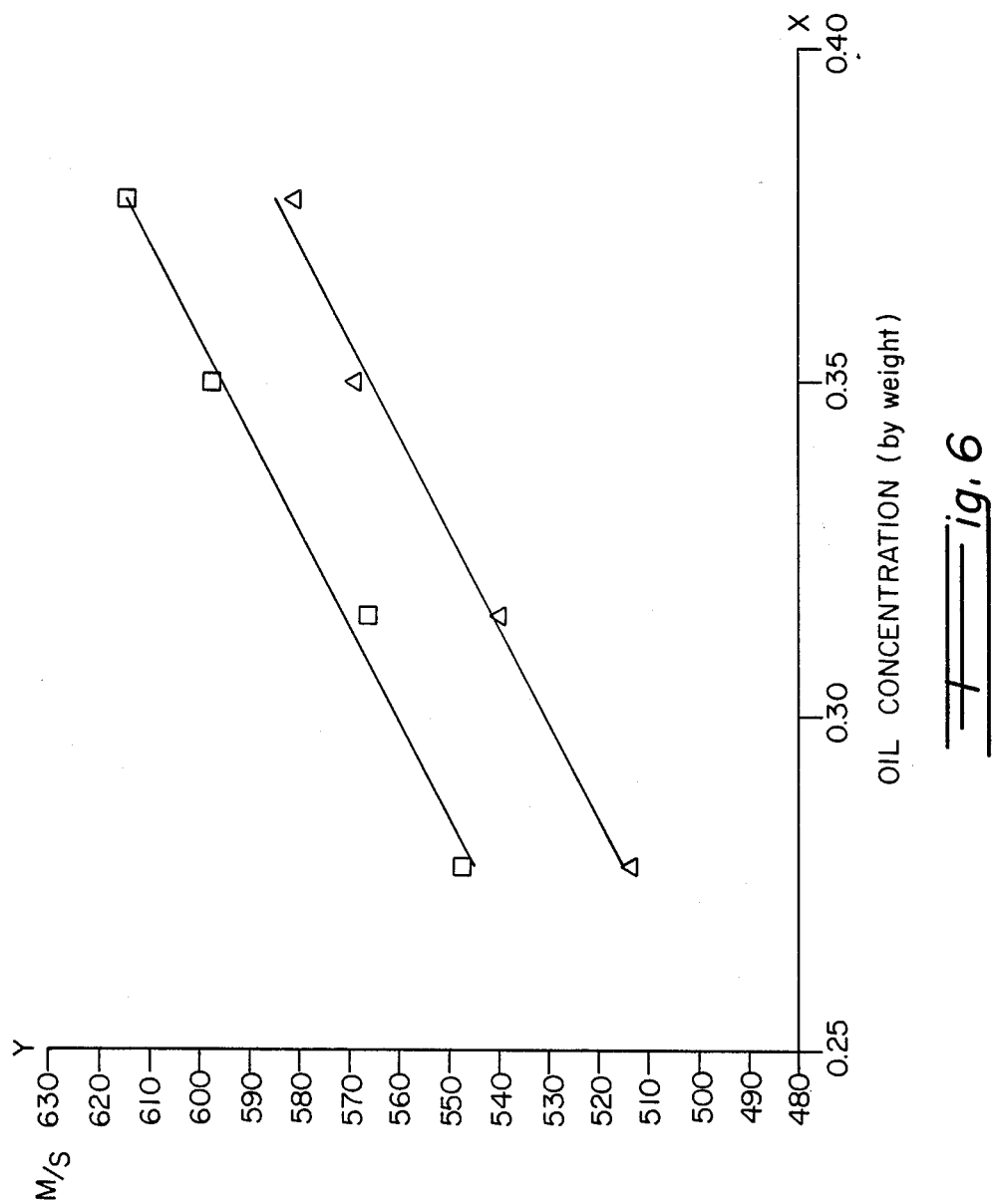
FIG. 6 is a graph showing the relationship of acoustic velocity in meters/second (m/s) of an acoustic wave in the refrigerant/lubricant mixture to the weight percent (%) of lubricant in the mixture, which is useful in understanding the present invention and in allowing the output meter of the system of FIG. 5 to be calibrated directly in weight percent.

The transducer 29a produces an acoustic pulse of energy which is coupled into the liquid mixture within the conduit 25 (FIGS. 1, 4A and 4B) via the wall of the conduit 25 and the layer of coupling compound positioned between the wall and the transducer 29a. The acoustic energy pulse is passed through the liquid mixture of lubricant and refrigerant within the conduit 25, passing along a path of predetermined length, determined by the spacing of the transducers 29a, 31a relative to one another. The acoustic energy pulse is coupled out of the liquid mixture, through the wall of the conduit 25 and the layer of coupling compound to the acoustic-to-electric transducer 31a. It is readily understandable that a time period expires from the instant the electric energy pulse is supplied to the transducer 29a to the instant an electric pulse is produced from the transducer 31a. A minor portion of the period can be attributed to the response time of the transducer 29a and 31a and to the thickness of the wall of the conduit 25, which are constants. The remaining, variable portion of the time period is attributed to the transit time of the ultrasonic pulse along the predetermined path in the liquid mixture within the conduit 25. Thus, any variation in the transit time is a function of the characteristics of the mixture. As a practical matter, given a temperature, the acoustic velocity of the acoustic pulse in the liquid mixture within the conduit 25 varies, as shown graphically in FIG. 6 in meters-per-second (M/S) along the y-axis for two different temperatures (25° C. and 30° C.). The actual laboratory test readings are illustrated as small squares, the respective characteristics being shown respectively are straight lines A and B, which are computer-fit curves based on the gathered data. The oil concentration (by weight) of the liquid refrigerant-lubricant mixture is shown along the x-axis. The relationship between oil concentrations and velocity are linear at both temperatures. In conducting the experiment to derive the graphically represented characteristics shown as lines A and B of FIG. 6, 8 ounces of 150 SUS naphthenic oil was mixed with 34 ounces of commercially available refrigerant sold under the designation R-12 as a starting mixture. The ending mixture consisted of 16 ounces of 150 SUS napthenic oil and 42 ounces of the refrigerant R-12. The material used for intermediate points consisted of portions of the starting and ending mixtures. It is to be understood that any number of various commercially available refrigerants could be used instead of R-12, including many forms of fluorocarbons and refrigerants sold under the trademark FREON ®. Lubricants other than SUS 150 naphthenic oil could be used.

Returning to FIG. 5, a portion of the pulse of electric energy from the gate 71 is fed, via a coupling capacitor 73, to a rectifier 74 which provides a d.c. output across a capacitor 76 shunted by a resistor 75. The d.c. pulse which appears across the RC circuit constituted by the resistor 75 and the capacitor 76 is fed to a first differentiating circuit constituted by a series connection to circuit ground defined by a capacitor 77 and a resistor 78, a short voltage spike corresponding to the leading edge of the pulse appearing across the RC circuit 75, 76 is produced across the resistor 78.

In similar fashion, the a.c. pulse produced by the receiving acoustic-to-electric transducer 31a is fed, via a coupling capacitor 81, to a rectifier 82 which produces a d.c. output across a capacitor 83 shunted by a resistor 84. The d.c. pulse which appears across the RC circuit constituted by the capacitor 83 and the resistor 84 is fed to a second differentiating circuit constituted by a series connection to circuit ground defined by a capacitor 85 and a resistor 86. A short voltage spike corresponding to the leading edge of the pulse appearing across the RC circuit 83, 84 appears across the resistor 86.

The respective voltage spikes which appear respectively across the resistors 78 and 86 are fed respectively to the ENABLE and RESET input terminals of a counter 79 which has its CLOCK input connected to a clock pulse source 80. In operation, whenever the voltage spike (which indicates the occurrence of the leading edge of an input energizing pulse to the transducer 29a) appears across the resistor 78, the counter 79 starts to count the regularly occurring clock pulses from the clock pulse source 80 and continues so to do until the voltage spike (which indicates the occurrence of the leading edge of an ultrasonic pulse received by the acoustic-to-electric transducer 31a) appears across the resistor 86 which resets the counter 79. The pulse count from the counter 79 is supplied to a pulse-to-amplitude converter 87 which, in turn, provides an output signal to a meter 88 calibrated to read in weight percent, velocity or refrigerant-to-lubricant ratio. Thus, the weight percent of the oil in the mixture of lubricant and refrigerant or the like can be read and a determination whether or not of the ratio is within acceptable limits prevails. If desired the meter 88 could be of the type that holds its maximum deflection until reset, making it easy to read.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A system for measuring refrigerant-to-lubricant ratio of a liquid within a conduit having a wall and constituting a portion of an enclosed-flow air-conditioning or refrigerating apparatus which includes a compressor, a condenser, an evaporator and an expansion work-load means, the system being operative to transmit and to receive ultrasonic energy to and from a portion of the conduit in which refrigerant in the apparatus is in a liquid state between the evaporator and the expansion-work-load means intermediate the condenser and the evaporator, and wherein the system comprises means for generating at least-one pulse of ultrasonic energy, means for coupling the at-least-one pulse of ultrasonic energy via the wall into a path of substantially-predetermined length and having an end within the liquid in the conduit, means for coupling the at-least-one pulse of ultrasonic energy via the wall from the end of the path of substantially-predetermined length, as received at the end thereof, and means responsive to the at-least-one ultrasonic pulse as transmitted and received for determining velocity of the ultrasonic pulse within the liquid in the conduit as a measure of the ratio of refrigerant to lubricant by volume in the conduit.

2. The system according to claim 1, wherein said means responsive to the at-least-one ultrasonic pulse as transmitted and received includes readout means calibrated in percent of lubricant in the liquid by volume as a function of weight and speed of travel of the at-least-one pulse within the liquid portion of the conduit.

3. The system according to claim 2 wherein the means for generating at-least-one pulse of ultrasonic energy includes a first transducer coupled to the conduit, and the means responsive to the at-least-one ultrasonic pulse comprises a second transducer coupled to the conduit.

4. The system according to claim 1 wherein the means for generating at-least-one pulse of ultrasonic energy includes a first transducer coupled to the conduit, and the means responsive to the at-least-one ultrasonic pulse comprises a second transducer coupled to the conduit.

5. A system for measuring refrigerant-to-lubricant ratio of a liquid within an enclosed-flow air-conditioning or refrigerating apparatus which includes a compressor, a condenser, an evaporator and an expansion work-load means, the system being operatively positioned and arranged to pass at-least-one pulse of ultrasonic energy into and out from a portion of the conduit in which refrigerant in the apparatus is in a liquid state between the evaporator and the expansion-work-load means intermediate the condenser and the evaporator, the system comprising means for generating at-least-one pulse of ultrasonic energy, means for coupling the at-least-one pulse of ultrasonic energy into a path of substantially-predetermined length within the liquid in the conduit, means for coupling the at-least-one pulse of ultrasonic energy from the path of substantially-predetermined length, and means for determining velocity of the ultrasonic pulse within the liquid in the conduit as a measure of the ratio of refrigerant to lubricant by volume in the conduit.

6. The system according to claim 5 wherein said means for determining velocity of the ultrasonic pulse within the liquid includes readout means calibrated in percent of lubricant in the liquid by weight.

7. The system according to claim 6 wherein the apparatus includes a conduit containing some of the liquid and the means for generating at least one pulse of ultrasonic energy comprises a first transducer coupled to the conduit and the means responsive to the ultrasonic pulse comprises a second transducer coupled to the conduit.

8. The system according to claim 5 wherein the apparatus includes a conduit containing some of the liquid, the means for generating at least one pulse of ultrasonic energy comprises a first transducer coupled to the conduit and, the means responsive to the ultrasonic pulse comprises a second transducer coupled to the conduit.

9. A method of measuring liquid refrigerant-to-lubricant ratio in an enclosed-flow air-conditioning or refrigerating apparatus, the method comprising:
   generating a pulse of ultrasonic energy;
   coupling the pulse of ultrasonic energy into a path of predetermined length which has an end within the liquid;
   coupling the pulse of ultrasonic energy from the end of the path of predetermined length within the liquid; and
   determining the velocity of the ultrasonic pulse within the liquid from its transit time along the path of predetermined length.

10. The method according to claim 9 and including determining from the said velocity of the ultrasonic pulse the percent of lubricant in the liquid by volume.

11. The method according to claim 10 and including providing the path in the liquid with a conduit forming part of the air-conditioning or refrigerating apparatus.

12. The method according to claim 9 and including providing the path in liquid with a conduit forming part of the air-conditioning or refrigerating apparatus.

* * * * *